(12) United States Patent
Jansen

(10) Patent No.: US 6,824,513 B2
(45) Date of Patent: Nov. 30, 2004

(54) DEVICE, METHOD AND USE OF AN ODOR DETECTION UNIT FOR EXAMINING AND/OR RECORDING

(75) Inventor: Klaus Jansen, Buxtehude (DE)

(73) Assignee: Thomas Hilfen Hilbeg GmbH & Co. KG, Bremervorde (DE)

( * ) Notice: Subject to any disclaimer, the term of this patent is extended or adjusted under 35 U.S.C. 154(b) by 73 days.

(21) Appl. No.: 10/168,895

(22) PCT Filed: Dec. 22, 2000

(86) PCT No.: PCT/EP00/13150

§ 371 (c)(1),
(2), (4) Date: Oct. 2, 2002

(87) PCT Pub. No.: WO01/48473

PCT Pub. Date: Jul. 5, 2001

(65) Prior Publication Data

US 2003/0056569 A1 Mar. 27, 2003

(30) Foreign Application Priority Data

Dec. 23, 1999 (DE) ........................................ 199 62 808

(51) Int. Cl.⁷ ................................................. A61B 5/00
(52) U.S. Cl. ..................... 600/300; 128/898; 340/573.1
(58) Field of Search ................................ 600/300–301, 600/587, 595, 529, 532; 340/539.1, 573.1, 583.4, 825.49; 128/903, 904, 920, 898; 73/23.34; 379/38

(56) References Cited

U.S. PATENT DOCUMENTS 6,234,006 B1 * 5/2001 Sunshine et al. ........... 600/532

FOREIGN PATENT DOCUMENTS

| DE | 38 23 736 C2 | 2/1898 |
| DE | 693 15 855 T2 | 6/1994 |
| DE | 684 16 842 T2 | 3/1995 |
| DE | 195 22 774 A1 | 1/1997 |
| DE | 197 30 733 A1 | 2/1999 |
| EP | 0 699 414 A1 | 3/1996 |

OTHER PUBLICATIONS

German Language copy of the PCT International Search Report.
German Language copy of the German Patent Office Search Report issued on the German National Phase version of the patent application.
Dickinson, T.A et al., "Current Trends in 'Artificial–Nose', Technology", TIBTECH, Jun. 1998 (vol. 16.), pp. 251–258.

* cited by examiner

Primary Examiner—Max F. Hindenburg
Assistant Examiner—Michael Astorino
(74) Attorney, Agent, or Firm—Technoprop Colton LLC

(57) ABSTRACT

The invention relates to a device and method for examining and/or recording medical disorders, physical conditions and/or physiological processes of a test person or patient. The inventive device comprises a sensor unit and a display unit for indicating a sensor signal that is generated and/or processed by the sensor unit, whereby the sensor unit can be placed in the vicinity of test persons or patients. This is particularly advantageous in the field of nursing care in order to be able to monitor the quantity and quality of treatment. To this end, an odor detection unit is provided for measuring odors. By virtue of the fact that examination is carried out in a non-contact manner, measurements can be continuously taken without causing harm to the test person.

20 Claims, No Drawings

DEVICE, METHOD AND USE OF AN ODOR DETECTION UNIT FOR EXAMINING AND/OR RECORDING

DESCRIPTION

The invention relates to a device for examining and/or recording human medical disorders, in particular inflammations in the cutanous and/or subcutaneous region, physical conditions and/or physiological processes of a person (test person or patient). The device comprises a sensor unit and an display unit for indicating a sensor signal that is generated and/or processed by the sensor unit, it being possible to assign the sensor unit to the person with no influence being exerted on the latter.

Furthermore, the invention relates to a method for examining and/or recording human physical disorders, in particular inflammations in the cutaneous and/or subcutaneous region, physical conditions and/or physiological processes of a person, with a sample being examined by means of a sensor unit. In addition, or alternatively, the sensor unit can be used to detect the odor of essentially the person's entire body. The invention provides for displaying a sensor signal generated and/or processed by the sensor unit, with the sensor unit being placed in the region of the test person or patient.

Finally, the invention relates to preferred uses of an odor sensor unit, specifically and in particular for prophylaxis, the early detection of diseases, ascertaining the immune status, ascertaining the activity of the immune system or of the immune status and/or ascertaining the risk of thrombosis.

In the field of nursing care, particularly that of the elderly, there exists in many cases a significant deficit in nursing staff. The result of this is that personnel employed in this field are frequently overworked and thus lack the necessary motivation. Required nursing tasks are therefore neglected or performed unsatisfactorily. For this reason there is an expressed need for monitoring the daily tasks involved in nursing care. Monitoring by video cameras is questionable due to reasons of data privacy. On the other hand, a oral survey of the nursing-care patients is also problematical as they are either incapable of providing a concise and objective answer or provide inaccurate or untruthful responses due to their dependency on the nursing staff.

The invention is therefore based on the technical problem of improving the monitoring and/or treatment of individuals (test persons or patients).

The invention's solution to this problem is disclosed in the features of the independent claims. A device of the kind introduced above is characterized for the solution of this problem in that the sensor unit is an odor sensor unit that does not disturb or otherwise influence the individual involved. Thus the monitoring or examination of the individual places no demands on the individual or the nursing staff. The individual does not need to participate actively in the monitoring and/or examination.

The method referred to above is characterized in that the sensor unit is employed to investigate at least one odor sample and/or in essence the entire body of a person. Furthermore, the problem is solved by employing at least one odor sensor unit for prophylaxis or the early detection of physical disorders, in particular as an indication of immune system activity, for example the risk of thrombosis and/or for investigating bacterial or viral illnesses. But the invention can also be employed to examine and/or record inflammations in the cutaneous or subcutaneous region.

The invention is based on the knowledge that the human body exudes different odorants depending on its physical state, whereby these odorants can originate at different points of the body. For this reason, it is preferable to ascertain the odor of the entire body or at lease a significantly large proportion of the body. These odorants, although produced at even the slightest of somatic changes, are in many cases present at such extremely low concentrations that they are practically imperceptible by humans.

The invention therefore employs a sensitive "artificial nose", namely a odor sensor unit for ascertaining and examining the odorants. Based on the measured odorants—and a subsequent thorough evaluation —it is possible to draw conclusions concerning the body's current physical state. In particular, however, conclusions about the body's state of health or alterations in it can also be drawn from changes in the concentration of (various) odorants. On the whole, the measured odorants or the measured expression of olfactory information provide essential data concerning genetic and/or physiological states as well as those concerning immunological processes in the organism. This opens up many fields of application, in particular those related to the examination and monitoring of the persons in long-term care, patients or test persons in general.

In addition, the invention is especially employed for recording the progress of nursing care treatment or the course of any other illness. Due to changes in odorant concentration it is possible to draw conclusions about whether the present state will improve, deteriorate or remain the same.

Furthermore, the invention can also be used advantageously for determining stages of sleep as well as other physiological processes during sleep. It can be used to study new findings on sleep patterns in general as well as the individual sleep phases of test persons.

In addition, the invention can also be used to monitor any healing process occurring during illness, for example that of an ulcer, in particular a decubitus ulcer. The invention can also be employed for the observation of other types of inflammation in the cutaneous and/or subcutaneous region and their origin. This even provides the possibility of administrating targeted prophylactic and therapeutic measures. Thus any necessary therapy can be established in agreement with the respective healing process, i.e. optimized in the course of ongoing phases. The indication of the measured odorant also provides an interim result which can be evaluated for optimization measures and can also be employed in a diagnosis.

Preferably a sensor unit has a sensor array, in particular an odor sensor array comprising a plurality of individual gas sensors, which react differently to specific odorants. Thus when examining an odor sample one obtains a number of sensor signals corresponding to the number of gas sensors. By distributing the odor sensors over an appropriate surface area it is possible to ascertain and evaluate the necessary, preferably entire, body surface odor.

Preferably the sensor signal(s) should be recorded continuously in order to detect any changes. By means of the further preferred use of multiple odor sensor units it is also possible to observe specific local or global changes in the test person odor and/or the emergence of a specific test person odor.

The information obtained can be used, for example, for tracing the genesis of a decubitus ulcer—which in particular can arise due to negligent nursing care—or for the early thrombosis detection. This makes it possible to administer counteractive measures in an advantageous manner. The detection of even trace odorants thus allows for the early detection of decubitus, for example.

Furthermore, dermal irritations can also be recognized. Preferably for this reason the invention makes it possible to trigger a specific alarm signal when a certain limit value is reached or exceeded in order to administer further examination procedures or any necessary treatment.

Further details of the invention can be taken from the subclaims and the exemplary embodiment, described below, of a monitoring system with a odor sensor unit.

Pursuant to an exemplary embodiment, an electronic sensor unit is employed. It is compact in design and is capable of delivering rapid results, i.e. within a few seconds or minutes. The sensor unit has a gas sample receiving unit, a sensor array and an evaluation unit. This makes it possible to account for the entire body odor of individuals in prophylactics and/or early detection of illnesses.

The sensor array comprises a plurality of semiconductor gas sensors, for example, ten such gas sensors. The gas sensors are spaced apart in such a manner that they are able to detect odors at different locations of the body. In particular, the gas sensors are arranged with a view to detecting odors from the entire body by scanning the entire body for odors. These semiconductor gas sensors are non-specific sensors which alter their electrical resistance in the presence of gaseous compounds. But the sensors are not identical. They vary by the use of different semiconductors, by different dopant concentrations and by different operating temperatures. The sensors therefore deliver different signals in the presence of the corresponding gaseous compounds. The detection limits of the sensors lie in the ppb- or ppm-range, i.e. in the range of $1:10^9$ or $1:10^6$, or even below, for example in the range of $1:10^{10}$ to $1:10^{12}$.

The intensity of the sensor signals is proportional to the concentration of the odorants, in particular of organic compounds, in the ambient air. One can to therefore obtain not only qualitative but also quantitative information about the odorants exuded by the body.

The sensors of a sensor array provide a characteristic sample in the presence of a gaseous compound. By making a comparison with previous samples it is therefore possible to identify particular substances. But such a comparison with previously identified values also provides information about the change in the composition of an odor. In particular, it is possible to determine whether individual compounds increase or decrease in their concentration.

The gas to be measured in the test is introduced into a sensor chamber, measuring approximately 1 to 2 ml, for about 20 seconds. After measurement has been completed the test chamber can be purged by a counterflow of purified air, preferably for an interval of approximately 40 seconds. The purging air can be taken from the ambient air which has been purified by an active charcoal filter. Preferably, this filter is also located in the housing of the sensor unit.

Due to sensor sensitivity, however, it is also possible to take measurements without using a test chamber and having to purge it in that the sensor is simply placed in the ambient air of the test person. In this case, however, the test results are less accurate but on the other hand the device as a whole is less cumbersome, smaller and less prone to malfunction.

The continuously measured signals are recorded with a recording unit. The record can be written to an electronic data storage medium or, in simpler cases, on an electromagnetic plotter. By virtue of this continuous-mode recording it is possible to establish any trend, in particular the increase or decrease of a substance.

The described electronic sensor unit is also capable of detecting complex mixtures of gaseous compounds. In particular, deviations from standard values can be detected immediately. The measured values can be further processed using mathematical methods. In particular, use is made here of distance classifiers (Euclid, correlation), factor analysis or artificial neuronal networks (corona effect).

Compared to the human nose, the electronic sensor unit has the advantage that it is considerably more sensitive and yields objective results, i.e. independent of the momentary judgment of a person. Furthermore, the electronic sensor unit remains unaffected by fatigue or distraction.

The described sensor unit is disposed in an area relative to the person under examination such that it does not disturb or otherwise influence the person. In addition, the sensor unit can be placed so that it is not noticed by the person at all. The sensor unit is preferably arranged in the region of a bed. The most appropriate position in this case is one located on or in the mattress or bed frame, or between the mattress and an upper bed. Preferably a plurality of sensor units are arranged at different position, in particularly across the surface area of the bed or mattress, and positioned in either an equal or unequal pattern of distribution. This distribution pattern usually selected should make it possible to determine the odor of the entire body, with gas sensors being particularly targeted to those positions of the body where one might expect a particularly characteristic odor. This makes it possible to localize different sources of odor over the entire body of the individual, thus obtaining information on the site of potential or already existing acute inflammation or the like in the test person.

The measured results thus obtained are shown on a display unit either immediately or after pre-processing, for example by employing analytical mathematical methods. This display allows an operator familiar with the monitoring system to evaluate the measured values as an intermediate result for diagnostics. Furthermore, in case one or more sensor signals reach, exceed or drop below a specified limit value, an alarm signal can be generated in order to notify someone from the nursing staff.

It is also possible to evaluate the odor-based measurements with other measured data or signals. For example, imprints left in the mattress, or other components of the bed, stretcher or the like, by the force of the person lying there can be compared to the measured odorant values. Such imprints or pressure sites are preferably measured at the position the odor has also been ascertained, i.e. in the region of all, or at least selected, gas sensors.

The invention makes it possible to determine the physiological, chemical or physical states of a non-injured body by non-invasive means. This makes any physical intervention in the test person unnecessary. Instead, the examination is conducted with no contact being made with the person. This advantage makes it possible to conduct measurements on a continual and long-term basis, practically for days, weeks or months at a time without disturbing or otherwise affecting the test persons.

Particularly in the field of nursing care, the described olfactory monitoring system can be used to monitor the quality of nursing treatment in a passive manner, i.e. without requiring the assistance of the person involved or otherwise disturbing said person. If an orderly forgets to move a bed-ridden patient on a regular basis, this will result in decubitus. By using the described monitoring system it is possible to identify an immanent decubitus in advance and thus prevent its formation. In particular, the described system can be used to determine whether the nursing staff is fulfilling its proper duties. The permits an objective evaluation of the quality of a nursing care institution. The invention thus offers a variety of uses in non-therapeutic fields of application.

What is claimed is:

1. Device for examining and/or recording medical disorders in humans, in particular inflammations in the cutaneous and/or subcutaneous region, physical conditions and/or physiological processes of a test person or patient, said device comprising a sensor unit and a display unit for indicating a sensor signal that is generated and/or processed by the sensor unit, it being possible to place the sensor unit in the region of the test person or patient characterized in that the sensor unit is a odor sensor unit which does not influence or otherwise interfere with the person involved and by a recording unit for the continuous recording of sensor signals.

2. Device according to claim 1 characterized by an evaluation unit for evaluating a current or recorded sensor signal, in particular for comparing the value of a sensor signal with other previously recorded values, and for the output of a result, in particular a result indicating improvement, deterioration or a condition that remains the same.

3. Device according to claim 2, characterized in that the evaluation unit has a comparison unit for comparing samples of the sensor signals of a sensor array with previously stored samples.

4. Device according to claim 1, characterized in that one or more sensors are positioned on or in the region of a bed, in particular a mattress or bed frame, and are distributed over a significant surface area of same.

5. Application of an odor sensor unit according to claim 1 for examining and/or recording medical disorders in humans for the prophylactics and/or early detection of human illnesses.

6. Application of an odor sensor unit according to claim 1 for examining and/or recording inflammations in the cutaneous and/or subcutaneous region of the in particular human body.

7. Application of an odor sensor unit according to claim 1 for determining the immune status and/or activity of the immune system and/or viral disorders and/or bacterial disorders of the human body.

8. Device for examining and/or recording medical disorders in humans, in particular inflammations in the cutaneous and/or subcutaneous region, physical conditions and/or physiological processes of a test person or patient, said device comprising a sensor unit and a display unit for indicating a sensor signal that is generated and/or processed by the sensor unit, it being possible to place the sensor unit in the region of the test person or patient characterized in that the sensor unit is a odor sensor unit which does not influence or otherwise interfere with the person involved and the sensor unit has a sensor array with in particular a plurality of gas sensors.

9. Device according to claim 8, characterized in that some or all gas sensors react differently to odorants, in particular by altering their electric resistance.

10. Device according to claim 8, characterized in that the gas sensors of a sensor unit exhibit different semiconductors, dopant concentrations and/or operating temperatures.

11. Method for examining and/or recording medical disorders in humans, in particular inflammations in the cutaneous and/or subcutaneous region, physical conditions and/or physiological processes of a test person or patient, with a sample being examined by means of a sensor unit and a sensor signal generated and/or processed by the sensor unit being displayed, with the sensor unit being positioned in the region of the test person or patient characterized in that at least one odor sample can be examined with the sensor unit and the sensor signal is recorded continuously and is compared with a previously recorded sensor signal or reference signal in order to establish any tendency of the sensor signal.

12. Method according to claim 11, characterized in that that a plurality of odor samples are taken and investigated, and at least a portion of the odor samples are compared to other measured values for the body.

13. Method according to claim 12, characterized in that that the odor samples are taken in the region of a bed.

14. Method for examining and/or recording medical disorders in humans, in particular inflammations in the cutaneous and/or subcutaneous region, physical conditions and/or physiological processes of a test person or patient, with a sample being examined by means of a sensor unit and a sensor signal generated and/or processed by the sensor unit being displayed, with the sensor unit being positioned in the region of the test person or patient, characterized in that at least one odor sample can be examined with the sensor unit and at least one odor sample of the essentially entire body surface area is examined by means of a sensor array with different gas sensors.

15. Method for examining and/or recording medical disorders in humans, in particular inflammations in the cutaneous and/or subcutaneous region, physical conditions and/or physiological processes of a test person or patient, with a sample being examined by means of a sensor unit and a sensor signal generated and/or processed by the sensor unit being displayed, with the sensor unit being positioned in the region of the test person or patient characterized in that at least one odor sample can be examined with the sensor unit and the sensor signal triggers an alarm signal upon reaching, exceeding or not reaching a limit value.

16. Method for examining and/or recording medical disorders in humans, in particular inflammations in the cutaneous and/or subcutaneous region, physical conditions and/or physiological processes of a test person or patient, with a sample being examined by means of a sensor unit and a sensor signal generated and/or processed by the sensor unit being displayed, with the sensor unit being positioned in the region of the test person or patient characterized in that the odor of essentially the entire body of the person is determined by the sensor unit and the sensor signal is recorded continuously and is compared with a previously recorded sensor signal or reference signal in order to establish any tendency of the sensor signal.

17. Method according to claim 16 characterized in that that a plurality of odor samples are taken and investigated and at least a portion of the odor samples being compared to other measured values for the body.

18. Method according to claim 17 characterized in that that the odor samples are taken in the region of a bed.

19. Method for examining and/or recording medical disorders in humans, in particular inflammations in the cutaneous and/or subcutaneous region, physical conditions and/or physiological processes of a test person or patient, with a sample being examined by means of a sensor unit and a sensor signal generated and/or processed by the sensor unit being displayed, with the sensor unit being positioned in the region of the test person or patient characterized in that the odor of essentially the entire body of the person is determined by the sensor unit and at least one odor sample of the essentially entire body surface area is examined by means of a sensor array with different gas sensors.

20. Method for examining and/or recording medical disorders in humans, in particular inflammations in the cutaneous and/or subcutaneous region, physical conditions and/or physiological processes of a test person or patient, with a sample being examined by means of a sensor unit and a sensor signal generated and/or processed by the sensor unit being displayed, with the sensor unit being positioned in the region of the test person or patient characterized in that the odor of essentially the entire body of the person is determined by the sensor unit and the sensor signal triggers an alarm signal upon reaching exceeding or not reaching a limit value.

* * * * *